United States Patent
Bernhardt et al.

(10) Patent No.: US 7,817,834 B2
(45) Date of Patent: Oct. 19, 2010

(54) METHOD FOR OPERATING AN X-RAY DIAGNOSTICS DEVICE FOR GENERATING HIGH-RESOLUTION SUBTRACTION ANGIOGRAPHY IMAGES

(75) Inventors: Philipp Bernhardt, Forchheim (DE); Frank Deinzer, Röthenbach (DE); Peter Durlak, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 924 days.

(21) Appl. No.: 11/704,417

(22) Filed: Feb. 8, 2007

(65) Prior Publication Data

US 2008/0019479 A1 Jan. 24, 2008

(30) Foreign Application Priority Data

Feb. 10, 2006 (DE) ........................ 10 2006 006 451

(51) Int. Cl.
*G06K 9/00* (2006.01)
(52) U.S. Cl. ........................ 382/129; 382/276; 382/294; 382/299
(58) Field of Classification Search ................. 382/128, 382/130, 293, 294, 299
See application file for complete search history.

(56) References Cited

U.S. PATENT DOCUMENTS

| | | | |
|---|---|---|---|
| 4,973,111 A | | 11/1990 | Hascke et al. |
| 5,649,032 A | * | 7/1997 | Burt et al. .................... 382/284 |
| 6,426,994 B1 | * | 7/2002 | Van Vaals ................. 378/98.12 |
| 7,492,967 B2 | * | 2/2009 | Toki et al. .................... 382/299 |

FOREIGN PATENT DOCUMENTS

| | | |
|---|---|---|
| DE | 100 37 735 A1 | 2/2002 |
| DE | 10 2005 010 119 A1 | 11/2006 |

OTHER PUBLICATIONS

Astrid Franz et al.: "Modular Toolbox for Derivative-based Medical Image Registration", Proceedings of SPIE 2005, pp. 1222-1233, vol. 5747.
Sina Farsiu et al.: "Advances and Challenges in Super-Resolution", Invited Paper, International Jounial of Imaging Systems and Technology, Special Issue on High Resolution Image Reconstruction, 2004, pp. 47-57, vol. 14, No. 2.
Bernd Fischer et al.: "FLIRT: A Flexible Image Registration Toolbox", Biomedical Image Registration, Second International Workshop (WBIR) 2003, pp. 261-270, Lecture Notes in Computer Science, Band 2717.

(Continued)

*Primary Examiner*—Tom Y Lu

(57) ABSTRACT

The invention relates to a method for operating an x-ray diagnostics device having an x-ray source, an x-ray image detector and an image system for generating a subtraction angiography sequence, in which a subtraction angiography sequence of low resolution individual images containing moving structures is created, registration of the individual images one with another is performed, and the images in the subtraction angiography sequence are used to compute a high resolution image.

10 Claims, 5 Drawing Sheets

OTHER PUBLICATIONS

Sharon Peled et al.: "Superresolution in MRI: Application to Human White Matter Fiber Tract Visualization by Diffusion Tensor Imaging", Magnetic Resonance in Medicine, 2001, pp. 29-35, vol. 45.

M.Elad et al.: "Super-Resolution Reconstruction of Image Sequences", IEEE Transactions on Pattern Analysis and Machine Intelligence, 1999, pp. 817-834, vol. 21, No. 9.

M.Elad, A.Feuer: "Restoration of a Single Superresolution Image from Several Blurred, Noisy, and Undersampled Measured Images", IEEE Transactions on Image Processing, 1997, pp. 1646-1658, vol. 6, No. 12.

M.Irani et al: "Super Resolution from image sequences", International Conference on Pattern Recognition (ICPR 90), 1990, pp. 115-120.

A.Papoulis: "Generalized Sampling Expansion", IEEE Transactions on Circuits and Systems, 1977, pp. 652-654, vol. 24, No. 11.

* cited by examiner

18a

18b

18c

18d

18e

18f

18g

18h

18i

METHOD FOR OPERATING AN X-RAY DIAGNOSTICS DEVICE FOR GENERATING HIGH-RESOLUTION SUBTRACTION ANGIOGRAPHY IMAGES

CROSS REFERENCE TO RELATED APPLICATIONS

This application claims priority of German application No. 10 2006 006 451.8 filed Feb. 10, 2006, which is incorporated by reference herein in its entirety.

FIELD OF THE INVENTION

The invention relates to a method for operating an x-ray diagnostics device having an x-ray source, an x-ray image detector and an image system for generating a subtraction angiography sequence.

BACKGROUND OF THE INVENTION

An x-ray diagnostics device of this kind, known from German patent DE 100 37 735 A1, is shown as an example in FIG. 1. Said device has a support 1 supporting a rotatable C-arm 2 which has an x-ray emitter 3 and an x-ray image detector 4 attached to its ends.

As an alternative to the stand 1 shown, floor and/or ceiling mounted stands can also be used. The C-arm 2 can also be replaced by a C-arm 2 of the type known as an electronic C-arm 2, in which the x-ray emitter 3 and the x-ray image detector 4 are electronically coupled.

The x-ray image detector 4 can be a flat semiconductor detector, rectangular or square in form, and preferably made from amorphous silicon (aSi).

A patient support table 5 for recording a heart of a patient undergoing investigation for example is located in the beam path of the x-ray emitter 3. Connected to the x-ray diagnostics device is an image system 6 which receives and processes the image signals of the x-ray image detector 4.

High-resolution images in x-ray diagnostics are fundamental for a reliable and accurate diagnosis. The aim in this respect is to make even the smallest details visible in high quality resolution. The principal means of influencing image quality in x-ray diagnostics is via the administered x-ray dose. The x-ray dose, however, mainly influences the image noise in an x-ray image. In very general terms a high x-ray dose produces a noise-free image.

The use of flat image detectors (FD) generally has no direct influence on the resolution of an x-ray image. This aspect depends to a significant extent on the pixel resolution of the detector system.

So-called zoom formats on C-arm systems form the prior art for displaying a high resolution x-ray image. Instead of using the whole x-ray image detector to generate images, these methods use only a small part of the surface so that the image appears enlarged. However, this method eventually reaches its limit at the available resolution of the x-ray image amplifier (IA) or flat image detector (FD), in that it is unable to display anatomical details which are smaller than the resolution of which the x-ray image detector is physically capable. Even image interpolation methods, which use procedures such as bicubic interpolation to compute individual images up to a higher resolution, cannot bring out details which are too small to be seen.

The only solution for improving the resolution capability of IA and FD systems is to change the x-ray image detectors at considerable expense. This means that an improved x-ray image detector must provide for example 2048×2048 pixels instead of 1024×1024 pixels over the same area. However, this places great demands on the detector manufacturers, who have now reached the limits of what is technically possible at the present time, not to mention the costs that a new x-ray image detector entails. Furthermore the area of each individual pixel, which decreases with increasing resolution, has a direct influence on the x-ray quantum yield, and thus also on such matters as the noise content of the x-ray image for instance.

In summary, the technical options for increasing the pixel resolution are very limited.

For this reason, in an earlier patent application DE 10 2005 010 119.4 it was proposed that the source-image distance (SID) for present-day C-arm systems be changed so that an image sequence containing low resolution images is created using a different distance (SID), the coordinate systems are then aligned and a high resolution image known as a C-arm super-resolution image is computed from the said images. To generate super-resolution images, however, this solution requires this special recording process. But the x-ray systems used for diagnostic purposes are not generally C-arm systems, since the latter are too dear and have too many features to be used for making a normal x-ray image. The C-arm solution mentioned above—varying the SID—cannot be used in present-day simple systems, since such systems do not generally make provision for the SID to be varied.

A similar problem also occurs in other areas where images are recorded using common video and photographic cameras, for example. Technically the resolution of photographic cameras cannot be increased at will. In applications requiring a higher degree of detail in the images, such as satellite imaging and military surveillance, methods using a plurality of separate recorded images from which to compute a single high resolution image have been known for a considerable time under the generic term "super-resolution", as described for instance in "Advances and Challenges in Super-Resolution" by Sina Farsiu et al., Invited Paper, International Journal of Imaging Systems and Technology, Special Issue on High Resolution Image Reconstruction, Vol. 14, No. 2, pages 47 to 57, 2004.

In the medical field, the use of a super-resolution approach to the generation of high-resolution MRI images is described only in "Super-Resolution in MRI: Application to Human White Matter Fiber Tract Visualization by Diffusion Tensor Imaging" by Sharon Peled et al., Magnetic Resonance in Medicine, 45, pages 29 to 35 (2001).

The functional principle of super-resolution approaches is based on the premise that input is available in the form of an image sequence consisting of a plurality of images which can be registered against one another by a suitable, usually affine but also flexible transformation, that is, images having a suitable type of "movement". In the case of satellite imaging or video sequences recorded using a video camera, said suitable transformation may be achieved by a scene shift in the image. This translation fulfills the requirement for an affine transformation and is very easy to produce.

According to M. Elad et al., "Super-Resolution Reconstruction of Image Sequences" IEEE Transactions on Pattern Analysis and Machine Intelligence, Vol. 21, No. 9, pages 817 to 834, September 1999, the general model for super-resolution can be described as follows: Low resolution images $g_i$ in an image sequence result from the projection P of a high-resolution image f onto their image plane and the adjustment of their coordinate systems by an affine 2D transformation. Only the low resolution images can be observed—the high resolution image cannot be observed due to the limited capabilities of the camera. It follows from this that the images $g_i$ are all offset relative to one another and in fact must be offset for the approach to work.

The super-resolution principle will now be explained with the aid of FIG. 2. Each box, whether large or small, represents a single pixel. FIG. 2 shows a first low resolution image 7 having pixels 10 and a second image 8 shifted in the x and y directions and having the same low resolution, both images being intended for inclusion in a high resolution image 9 having pixels 11 my means of a transformation. The area of the pixels 11 in the high-resolution image 9 is small, and the area of the pixels 10 in the original low resolution images 7 and 8 is large in comparison.

The coordinate system offset necessary for super-resolution is very easy to create for satellite imaging and video recording:

With satellite imaging:
The satellite travels around the earth all by itself. The recorded images are therefore offset from one another.

With video recording:
A suitable movement can be introduced very simply on a manual basis.

In both cases therefore a shifted scene of low resolution images forms the raw material for a high-resolution image.

SUMMARY OF THE INVENTION

The object of the invention is to provide a method so that high resolution images of blood vessel systems showing the smallest details in the utmost clarity can be created on any x-ray device from dynamic image sequences.

This object is achieved in accordance with the invention in that
a subtraction angiography sequence of individual low resolution recordings containing rhythmically moving fine structures is created,
the individual recordings are registered relative to one another by means of transformation, and
the images of the subtraction angiography sequence are use to compute a high resolution image.

The use of a super-resolution approach on an x-ray device makes it possible to obtain an x-ray image quality with a degree of resolution which at the present time can be achieved only with difficulty using other technical options. This approach makes it possible to reveal anatomical structures or pathological changes that are simply too small for present-day x-ray image detectors. The blood vessel system has precisely those extremely small structures that cannot be seen in present-day images.

Advantageously a super-resolution image can be computed with the aid of an affine 2D transformation of the low resolution images.

According to the invention the method can include the following steps:
a) generating a series of x-ray images of a moving object,
b) selecting any preferred image as the reference image,
c) determining the optimum affine transformations $$T_i = \begin{pmatrix} 1 & 0 & 0 \\ k_{y,i} & 1 & 0 \\ 0 & 0 & 1 \end{pmatrix} \cdot \begin{pmatrix} 1 & k_{x,i} & 0 \\ 0 & 1 & 0 \\ 0 & 0 & 1 \end{pmatrix} \cdot$$

$$\begin{pmatrix} s_{x,i} & 0 & 0 \\ 0 & s_{y,i} & 0 \\ 0 & 0 & 1 \end{pmatrix} \cdot \begin{pmatrix} \cos(\alpha_i) & -\sin(\alpha_i) & 0 \\ \sin(\alpha_i) & \cos(\alpha_i) & 0 \\ 0 & 0 & 1 \end{pmatrix} \cdot \begin{pmatrix} 1 & 0 & x_i \\ 0 & 1 & y_i \\ 0 & 0 & 1 \end{pmatrix}$$

consisting of an angle of rotation and a translation within the image plane, a scaling ($s_{x,i}$, $s_{y,i}$) and a shear ($k_{x,i}$, $k_{y,i}$), in the x and y directions, for determining the parameters which map each image onto the reference image with minimal error, and
d) superimposing all the images by image reconstruction and computation of a super-resolution image.

It has proved to be advantageous for the angle of rotation, the translation, the scaling and the shear to be defined to subpixel accuracy.

According to the invention the method can also be described by the following steps:
a) generating a subtraction angiography sequence,
b) obtaining the necessary image offset,
c) selecting a region of interest,
d) selecting a suitable time segment,
e) registering the region of interest or the whole image, and
f) reconstructing a super-resolution image.

BRIEF DESCRIPTION OF THE DRAWINGS

The invention will be explained in greater detail below with the aid of exemplary embodiments shown in the drawings. These show the following.

DETAILED DESCRIPTION OF THE INVENTION

To use the above-mentioned super-resolution approaches for obtaining high-resolution images of the blood vessel system, it is necessary to find a way of producing an offset between the individual recorded images. Unlike the earlier patent application DE 10 2005 010 119.4, there is no intention to search for options that will enable super-resolution images to be generated. The intention is rather to keep the design and production cost of this solution within bounds.

Figure 1:
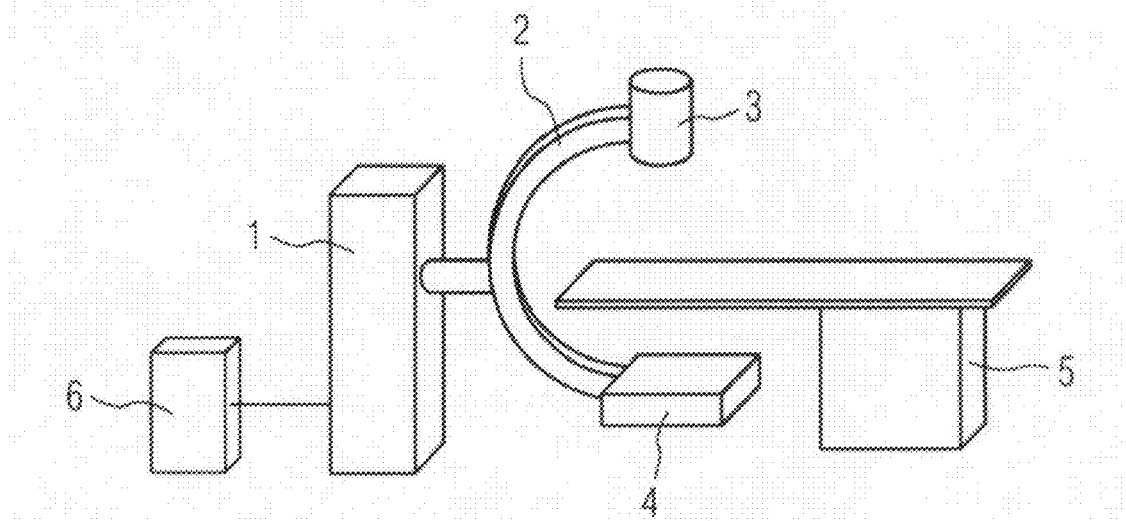
FIG. 1 A known x-ray diagnostics device,
FIG. 2 Symbolic images for explaining super-resolution,
FIG. 3 Part of an image system according to the invention,
FIG. 4 A subtraction angiography sequence,
FIG. 5 A selected region of interest from an image in the subtraction angiography sequence according to FIG. 4,
FIG. 6 An enlargement of the excerpt from FIG. 5, and
FIG. 7 The same excerpt from a high resolution super-resolution image.
Figure 2:
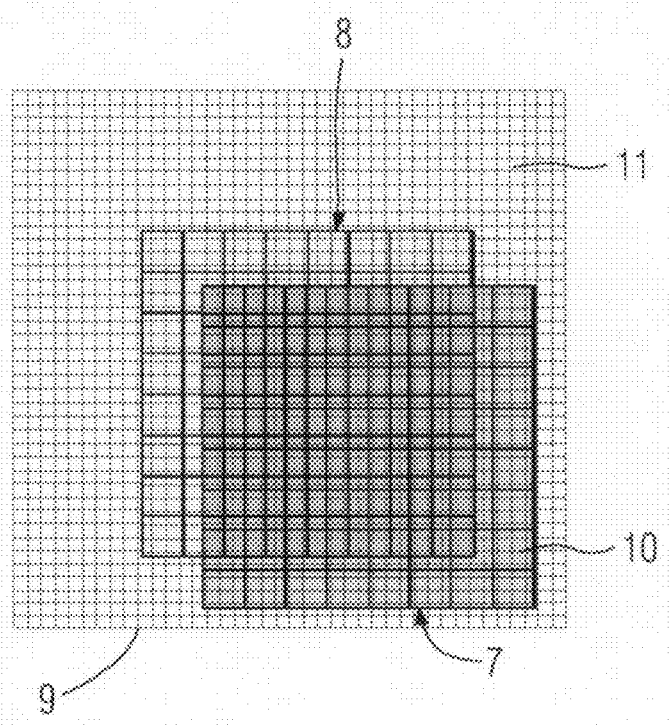
Figure 3:
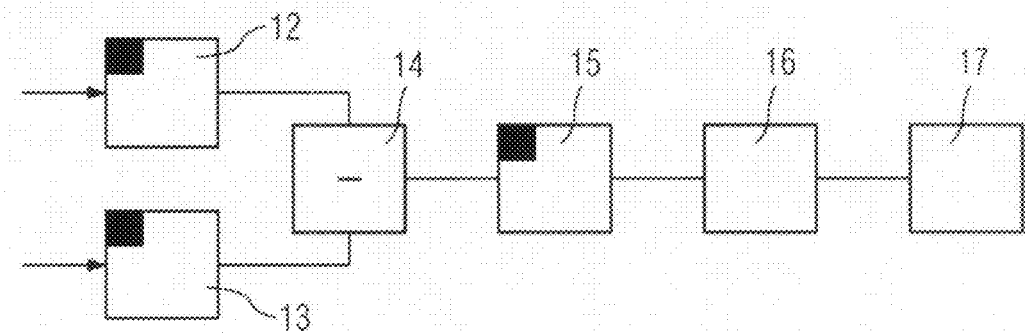

This is achieved by the configuration of the image system with the required characteristics shown in FIG. 3.

The digital signals from the x-ray images captured by the x-ray image detector 4 are fed to a first image memory 12 in which one or more empty pictures are stored. Following an injection of a radiopaque material (contrast medium), an angiography sequence of x-ray images including contrast medium, known as filling pictures, is captured by means of the detector 4 and saved in an image memory [13] for filling pictures. A subtraction stage 14 connected to the image memories 12 and 13 maps, either online or during offline postprocessing, the differences between the empty pictures and the filling pictures, this information being saved in an image memory 15 for subtraction pictures. To this image memory 15 is connected a registration stage 16 (described below) for registering the individual subtraction pictures, said registration stage being connected to a reconstruction stage 17 for generating a super-resolution image (described below).

Figure 4:
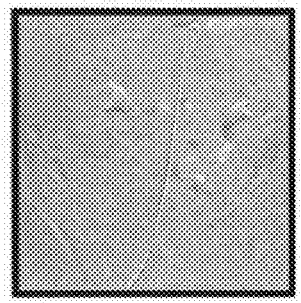
Figure 4:
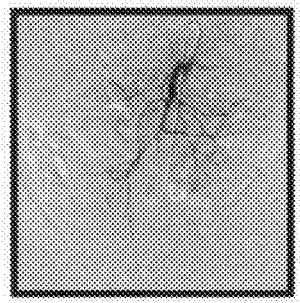
Figure 4:
Figure 4:
Figure 4:
Figure 4:
Figure 4:
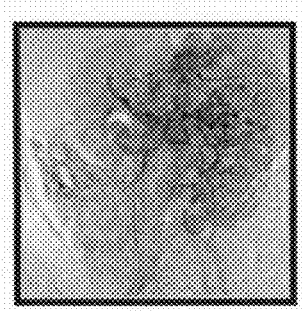
Figure 4:
Figure 4:

FIG. 4 shows a subtraction angiography sequence with individual images 18*a* to 18*i*, as they appear at the output from the subtraction stage 14 and are held in the image memory 15 for subtraction pictures.

The main sequence can be described as follows:
a) Generating a Subtraction Angiography Sequence:
First an x-ray image known as an empty picture is made of the region in the body being examined. A catheter or injection needle is then introduced into or upstream of the blood vessel of interest. When the contrast medium has been injected, further x-ray images are made in rapid succession. If these images are digitally stored, the empty picture can be subtracted from the angiography images. Unwanted pixels that are present on both images, such as bones, are thereby removed. This process is known as digital subtraction angiography. An example of an image sequence of this type is illustrated in FIG. 4, showing the individual images 18a to 18i, in which the contrast medium has advanced different distances.

b) Obtaining the Necessary Image Offset:

The main problem is to obtain the necessary movement in the image if said movement was not created mechanically. The theory states that movements in the subpixel range are sufficient. The actual patient does not move throughout the entire subtraction angiography, so no movement of the patient is present in the individual images 18a to 18i. On the other hand it can be observed that during subtraction angiography the blood vessel system itself moves under the influence of the blood flow to a very slight but sufficient extent. This movement is adequate for generating the super-resolution images. Once the stationary anatomical background has been removed by subtraction angiography, only the moving blood vessel structures remain visible in the image.

c) Selecting the Region of Interest:

In some circumstances a spatial region of interest in the subtraction angiography sequence has to be selected in cases where no transformation can be considered suitable enough out of all the images in the sequence, that is, from the whole visible region. An example of this can be seen in FIG. 5, in the case of the manually highlighted region of interest 19 in the subtraction image 18d. If an affine transformation can be used, the method described further on can be used. If on the other hand an affine transformation cannot be used, a flexible registration procedure can be used in such areas, for instance the methods described in the publications of Bernd Fischer et al., "FLIRT: A Flexible Image Registration Toolbox" in Biomedical Image Registration, Second International Workshop (WBIR) 2003, pages 261 to 270, Lecture Notes in Computer Science, Band 2717, Springer Verlag, Heidelberg, and Astrid Franz et al., "Modular Tool-box for Derivative-based Medical Image Registration" in Proceedings of SPIE 2005, Editors J. Michael Fitzpatrick, Joseph M. Reinhardt, Vol. 5747, pages 1222 to 1233, 2005. The problems arise because the movement of the blood vessel system in the image plane can be described by an affine transformation in only a limited region. Flexible registration can ease the problem but cannot solve it in every case, since blood vessel movements in opposite directions cannot be described in depth by these methods.

d) Selecting a Suitable Time Segment:

From the time sequence, select a time segment in which a constant filling level of the blood vessels predominates in the region of interest or in the entire set of images. As can be seen in FIG. 4, the blood vessels are not full at the beginning and end of the subtraction angiography sequence. These individual images 18a and 18i will not be used, since the content of the images must be as uniform as possible.

e) Registering the Region of Interest or the Whole Image:

A suitable method is used to register the consecutive individual images in the subtraction angiography sequence of the selected region of interest or of the whole visible region.

f) Reconstructing a Super-Resolution Image:

On the basis of the individual images 18b to 18h that have been registered in such a way, a super-resolution image in which the spatial 2D resolution is greater than that of the individual images can be computed from redundant information (a plurality of images show the same excerpt though their content is mutually offset). This step is generally known as image reconstruction, about which there is a whole range of publications in the literature:

The generalized sampling theorem, described by A. Papoulis in "Generalized Sampling Expansion", IEEE Transactions on Circuits and Systems, Vol. 24, No. 11, pages 652 to 654, November 1977.

The iterated back projection, described by M. Irani et al., in "Super resolution from image sequences", International Conference on Pattern Recognition (ICPR 90), pages 115 to 120, 1990.

The maximum likelihood method and the maximum a-posteriori probability method, described by M. Elad and A. Feuer in "Restoration of a Single Superresolution Image from Several Blurred, Noisy, and Undersampled Measured Images", IEEE Transactions on Image Processing, 6(12), pages 1646 to 1658, December 1997 and M. Elad et al., in "Superresolution reconstruction of an image", IEEE Transactions on Pattern Analysis and Machine Intelligence, 21, pages 817 to 834, 1999.

This image reconstruction can reveal details which are impossible to see in the individual images 18a to 18i, but which are visible in the super-resolution image due to the image reconstruction and the use of redundant information.

Figure 5:
Figure 6:
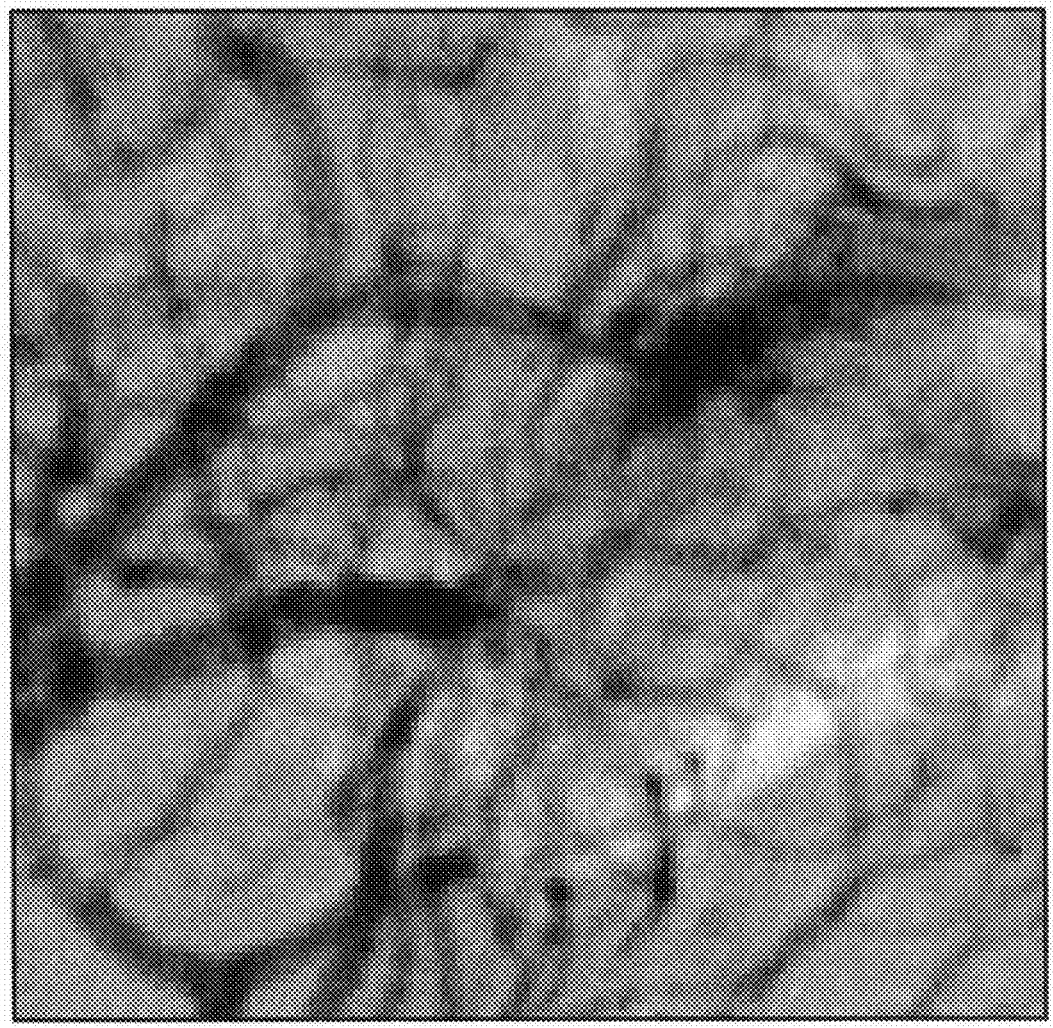
Figure 7:
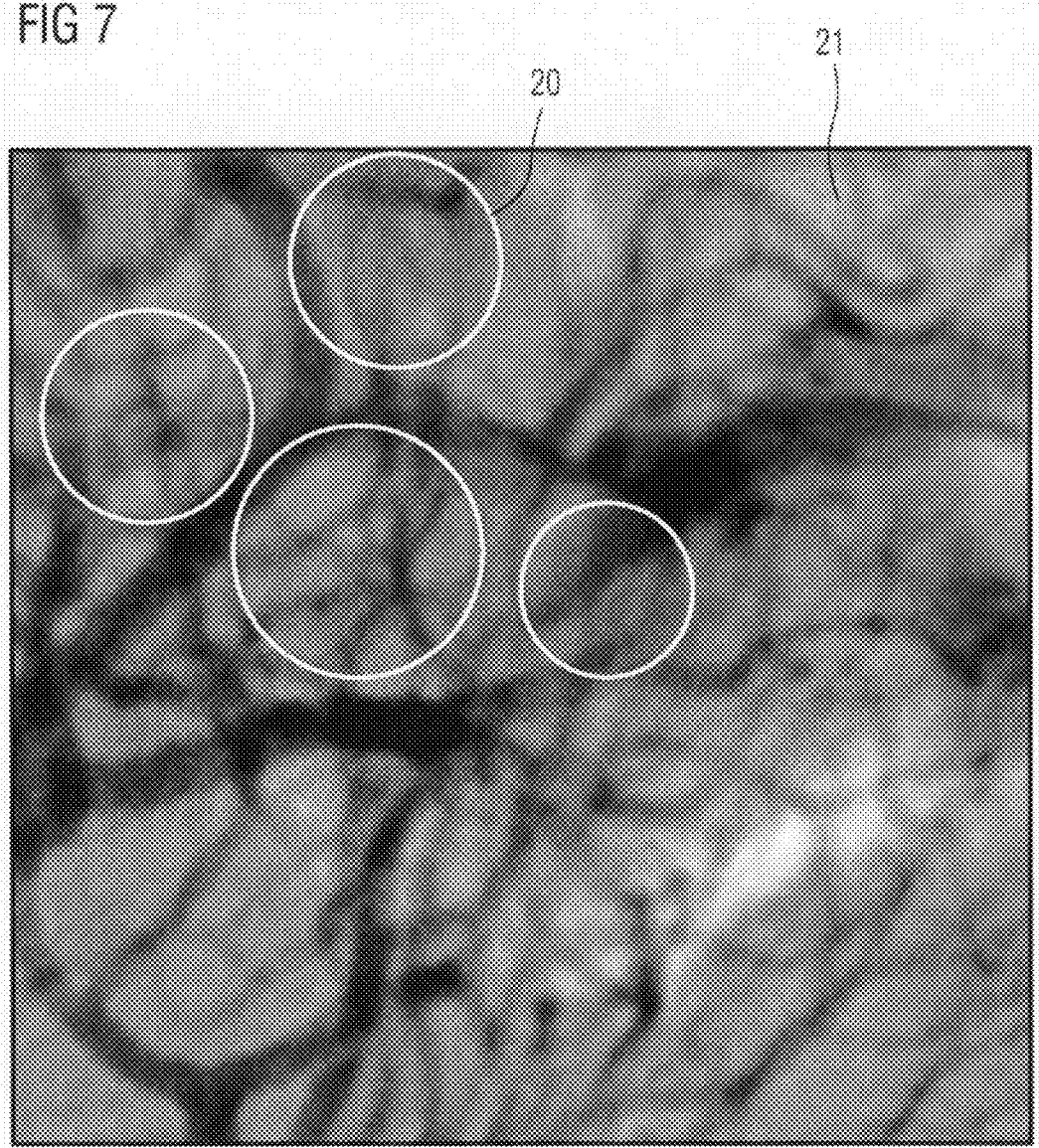

An example of the performance of super-resolution approaches in the blood vessel system which have occurred using the inventive method is shown in FIGS. 4 to 7. FIG. 4 shows some of the individual images 18a to 18i from the angiography sequence in 1024×1024 pixel format, as recorded nowadays using FD detectors. A high resolution image 21 is computed from said individual images 18a to 18i. The highlighted region of interest 19 in FIG. 5 is shown enlarged in FIG. 6. FIG. 7 shows the resulting super-resolution image 21. Even in the poor quality of a normal paper printout, it is possible to see significant improvements in the spatial resolution and a corresponding information gain. Many of the very fine structures can only be recognized in the image 21 in FIG. 7.

The method for registration by means of affine transformation is described below. Assume a series of individual images $g_i$ where $i=1$ to N, resulting from subtraction angiography, or regions of interest selected from said images. They are offset from one another by translation, rotation, scaling and shear.

The registration sequence takes the following form:

First select any preferred image $g_R$ as the reference image.

Define the optimal affine transformations $T_i$, $$T_i = \begin{pmatrix} 1 & 0 & 0 \\ k_{y,i} & 1 & 0 \\ 0 & 0 & 1 \end{pmatrix} \cdot \begin{pmatrix} 1 & k_{x,i} & 0 \\ 0 & 1 & 0 \\ 0 & 0 & 1 \end{pmatrix} \cdot$$

$$\begin{pmatrix} s_{x,i} & 0 & 0 \\ 0 & s_{y,i} & 0 \\ 0 & 0 & 1 \end{pmatrix} \cdot \begin{pmatrix} \cos(\alpha_i) & -\sin(\alpha_i) & 0 \\ \sin(\alpha_i) & \cos(\alpha_i) & 0 \\ 0 & 0 & 1 \end{pmatrix} \cdot \begin{pmatrix} 1 & 0 & x_i \\ 0 & 1 & y_i \\ 0 & 0 & 1 \end{pmatrix}$$

consisting of the angle of rotation ($\alpha_i$) and a translation ($x_i$, $y_i$) within the image plane, a scaling ($s_{x,i}$, $s_{y,i}$) and shear ($k_{x,i}$, $k_{y,i}$), in the x and y direction in each case. Said optimal transformation determines the parameters which map each image $g_i$ onto the reference image $g_R$ with minimal error.

For $g_R = g_i$ the following naturally applies:

$$T_i = \begin{pmatrix} 1 & 0 & 0 \\ 0 & 1 & 0 \\ 0 & 0 & 1 \end{pmatrix}$$

The important inventive points are:
- The physical blood vessels move on their own due to the blood flow.
- These blood vessels are revealed by means of a contrast medium.
- The stationary anatomical background is eliminated by creating a subtraction angiography sequence. Then only the moving blood vessels of interest are visible.
- Select a spatial region of interest.
- Select a suitable time segment from the sequence.
- Register the individual images of the selected region of interest in the given time segment relative to one another and create a super-resolution image on that basis.

FIG. 5 shows a normal x-ray image from the subtraction angiography sequence at a resolution of 1024×1024 pixels, as recorded using present-day FD detectors. The selected region of interest 19 highlighted is enlarged in FIG. 6 and shows the spatial resolution capability that can be achieved using a normal x-ray diagnostics device.

FIG. 7 shows the same excerpt, but taken from a computed super-resolution image after the described method has been used. Available to this super-resolution approach as input is a plurality of images having the quality shown in FIG. 6 and the required amount of movement, thus bringing about a significant improvement in the spatial resolution and a corresponding information gain. Considerably more and indeed finer structures can be recognized. Circles 20 highlight points at which the advantages of the super-resolution approach presented here are particularly significant.

During computation of the high resolution x-ray image 21, certain regions may have a different information content:
- Regions where movement cannot be discerned in any of the individual images 18a to 18i:
  - The resolution can of course be increased in such regions too, but there is no information gain. In other words no details are discernible that were not already discernible in the lower resolution individual images. Methods that can be used to enhance resolution include simple bilinear interpolation. It should however be noted that due to the relatively small range of movement in the SID these image regions are very small and the object of interest is also positioned more or less centrally by the examining doctor.
- Regions where movement can be discerned in all of the individual images 18a to 18i:
  - In these regions the information gain comes fully into its own. The effect is that in the excerpt from the x-ray image 21, details are revealed that cannot be seen in any of the individual images 18a to 18i.
- Regions where movement is present in some individual images—more than one but not all:
  - Generally speaking in this case the information gain (the improvement in resolution eventually discerned) increases in line with the available number of images of the region.

To sum up, the resolution of the high resolution x-ray image 21 is always uniformly great and in principle can be selected. The information content, i.e. the structures finally revealed, is dependent however on the amount of information available for a given region, that is, the number of low resolution x-ray images 18a to 18i in which movement can be perceived.

It has been shown that using a super-resolution approach on an x-ray device provides x-ray image quality at a resolution that enables a degree of detail currently unobtainable using other technical options. This approach makes it possible to reveal anatomical structures or pathological changes that are simply too small for present-day x-ray image detectors. The blood vessel system has precisely those extremely small structures that cannot be seen in present-day images.

An important advantage is that the necessary changes to x-ray equipment are easy to carry out, due to the fact that the arbitrary subtraction angiography sequences can be recorded on a daily basis just as they are at present, so that high resolution pictures can be generated from them. This process would be carried out as a postprocessing step as soon as the doctor has reviewed the sequences for diagnosis. The image reconstruction then required can easily be performed in the existing imaging system of the x-ray diagnostics device.

Significant advantages can be expected in the diagnostics of digital subtraction angiography, since structures exist with dimensions which, given the currently known x-ray diagnostics devices, can only be revealed by the inventive method.

The invention claimed is:

1. A method for operating an x-ray diagnostic device, comprising:
creating a subtraction angiography sequence comprising a plurality of low resolution x-ray images containing a moving structure of an object under diagnosis;
registering the x-ray images one with another by a transformation; and
computing a high resolution image based on the registered x-ray images,
wherein the registering comprises:
selecting a preferred image from the x-ray images as a reference image,
defining the transformation $T_i$ as $$T_i = \begin{pmatrix} 1 & 0 & 0 \\ k_{y,i} & 1 & 0 \\ 0 & 0 & 1 \end{pmatrix} \cdot \begin{pmatrix} 1 & k_{x,i} & 0 \\ 0 & 1 & 0 \\ 0 & 0 & 1 \end{pmatrix} \cdot$$

$$\begin{pmatrix} s_{x,i} & 0 & 0 \\ 0 & s_{y,i} & 0 \\ 0 & 0 & 1 \end{pmatrix} \cdot \begin{pmatrix} \cos(\alpha_i) & -\sin(\alpha_i) & 0 \\ \sin(\alpha_i) & \cos(\alpha_i) & 0 \\ 0 & 0 & 1 \end{pmatrix} \cdot \begin{pmatrix} 1 & 0 & x_i \\ 0 & 1 & y_i \\ 0 & 0 & 1 \end{pmatrix}$$

wherein $\alpha_i$ is an angle of rotation, $x_i$ and $y_i$ is a translation within an image plane, $s_{x,i}$ and $s_{y,i}$ is a scaling in x and y direction, and $k_{x,i}$ and $k_{y,i}$ is a shear in x and y direction, and
determining a parameter that map each image of the x-ray images onto the reference image with minimal error based on the transformation.

2. The method as claimed in claim 1, wherein the transformation is an affine 2D transformation.

3. The method as claimed in claim 1, wherein the angle of rotation, the translation, the scaling, and the shear are defined to subpixel accuracy.

4. A method for operating an x-ray diagnostic device to generate a super resolution image of an object under diagnosis, comprising:
creating a subtraction angiography sequence comprising a plurality of low resolution x-ray images containing a moving structure of the object;

obtaining a required image offset;

selecting a region of interest in the x-ray images;

selecting a time segment so that a constant filling level of the moving structure of the object is predominated in the region of interest;

registering the region of interest in the x-ray images one with another; and generating the super resolution image based on the registered x-ray images, wherein the registering is performed by a transformation comprising:

selecting a preferred image from the x-ray images as a reference image, defining the transformation $T_i$ as $$T_i = \begin{pmatrix} 1 & 0 & 0 \\ k_{y,i} & 1 & 0 \\ 0 & 0 & 1 \end{pmatrix} \begin{pmatrix} 1 & k_{x,i} & 0 \\ 0 & 1 & 0 \\ 0 & 0 & 1 \end{pmatrix} \cdot$$

$$\begin{pmatrix} s_{x,i} & 0 & 0 \\ 0 & s_{y,i} & 0 \\ 0 & 0 & 1 \end{pmatrix} \begin{pmatrix} \cos(\alpha_i) & -\sin(\alpha_i) & 0 \\ \sin(\alpha_i) & \cos(\alpha_i) & 0 \\ 0 & 0 & 1 \end{pmatrix} \begin{pmatrix} 1 & 0 & x_i \\ 0 & 1 & y_i \\ 0 & 0 & 1 \end{pmatrix}$$

wherein $\alpha_i$ is an angle of rotation, $x_i$ and $y_i$ is a translation within an image plane, $s_{x,i}$ and $s_{y,i}$ is a scaling in x and y direction, and $k_{x,i}$ and $k_{y,i}$ is a shear in x and y direction, and determining a parameter that map each image of the x-ray images onto the reference image with minimal error based on the transformation.

5. The method as claimed in claim 4, wherein the transformation is an affine 2D transformation.

6. The method as claimed in claim 4, wherein the angle of rotation, the translation, the scaling, and the shear are defined to subpixel accuracy.

7. The method as claimed in the claim 4, wherein the required image offset is a movement of the moving structure in the images.

8. An x-ray diagnostic device for generating a super resolution image of an object under diagnosis, comprising:

an x-ray source that emits an x-ray radiation passing through the object;

an x-ray detector that detects a plurality of x-ray images of the objects; and an imaging processing system that:

creates a subtraction angiography sequence the x-ray images containing a moving structure of the object, registers the x-ray images one with another by a transformation, and generates the super resolution image based on the registered x-ray images, wherein the imaging processing system registers the x-ray images by:

selecting a preferred image from the x-ray images as a reference image, defining the transformation $T_i$ as $$T_i = \begin{pmatrix} 1 & 0 & 0 \\ k_{y,i} & 1 & 0 \\ 0 & 0 & 1 \end{pmatrix} \begin{pmatrix} 1 & k_{x,i} & 0 \\ 0 & 1 & 0 \\ 0 & 0 & 1 \end{pmatrix} \cdot$$

$$\begin{pmatrix} s_{x,i} & 0 & 0 \\ 0 & s_{y,i} & 0 \\ 0 & 0 & 1 \end{pmatrix} \begin{pmatrix} \cos(\alpha_i) & -\sin(\alpha_i) & 0 \\ \sin(\alpha_i) & \cos(\alpha_i) & 0 \\ 0 & 0 & 1 \end{pmatrix} \begin{pmatrix} 1 & 0 & x_i \\ 0 & 1 & y_i \\ 0 & 0 & 1 \end{pmatrix}$$

wherein $\alpha_i$ is an angle of rotation, $x_i$ and $y_i$ is a translation within an image plane, $s_{x,i}$ and $s_{y,i}$ is a scaling in x and y direction, and $k_{x,i}$ and $k_{y,i}$ is a shear in x and y direction, and determining a parameter that map each image of the x-ray images onto the reference image with minimal error based on the transformation.

9. The x-ray diagnostic device as claimed in claim 8, wherein the angle of rotation, the translation, the scaling, and the shear are defined to subpixel accuracy.

10. The x-ray diagnostic device as claimed in claim 8, wherein the transformation is an affine 2D transformation.

* * * * *